(12) United States Patent
Gieselman

(10) Patent No.: US 6,441,092 B1
(45) Date of Patent: Aug. 27, 2002

(54) WET-STICK ADHESIVES

(75) Inventor: Melinda B. Gieselman, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/367,510

(22) PCT Filed: Jun. 18, 1999

(86) PCT No.: PCT/US99/13865

§ 371 (c)(1),
(2), (4) Date: Aug. 13, 1999

(87) PCT Pub. No.: WO00/78885

PCT Pub. Date: Dec. 28, 2000

(51) Int. Cl.[7] .............................................. C08L 33/00
(52) U.S. Cl. ....................... 525/191; 525/217; 525/218; 525/221; 525/222; 525/241; 428/41.3; 428/41.5; 428/355 CN; 428/355 AC; 524/442; 524/492; 524/500; 156/327; 156/330.9
(58) Field of Search ................................. 525/210, 217, 525/218, 221, 222, 241, 191; 462/901; 524/442, 492, 500; 156/327, 330.9; 428/41.3, 41.5, 355 CN, 355 AC

(56) References Cited

U.S. PATENT DOCUMENTS

| | | | |
|---|---|---|---|
| RE24,906 E | 12/1960 | Ulrich | 206/59 |
| 3,234,062 A | 2/1966 | Morris | 156/104 |
| 3,449,184 A | 6/1969 | Balk | 156/105 |
| 3,681,179 A | 8/1972 | Theissen | 161/4 |
| 3,772,262 A | 11/1973 | Clementi | 260/94.7 |
| 3,786,116 A | 1/1974 | Milkovich et al. | 260/885 |
| 3,842,059 A | 10/1974 | Milkovich et al. | 260/93.5 A |
| 3,867,222 A | 2/1975 | Plant et al. | 156/107 |
| 4,035,549 A | 7/1977 | Kennar | 428/409 |
| 4,181,752 A | 1/1980 | Martens et al. | 427/54.1 |
| 4,188,436 A | 2/1980 | Ellis et al. | 428/198 |
| 4,234,533 A | 11/1980 | Langlands | 264/261 |
| 4,299,639 A | 11/1981 | Bayer | 156/104 |
| 4,303,485 A | 12/1981 | Levens | 204/159.24 |
| 4,329,384 A | 5/1982 | Vesley et al. | 428/40 |
| 4,330,590 A | 5/1982 | Vesley | 428/336 |
| 4,341,576 A | 7/1982 | Lewis | 156/106 |
| 4,358,329 A | 11/1982 | Masuda | 156/106 |
| 4,362,587 A | 12/1982 | Baudin et al. | 156/87 |
| 4,379,201 A | 4/1983 | Heilmann et al. | 428/345 |
| 4,385,951 A | 5/1983 | Pressau | 156/105 |
| 4,386,991 A | 6/1983 | Shiomi et al. | 156/308.6 |
| 4,431,471 A | 2/1984 | Mertens et al. | 156/103 |
| 4,452,840 A | 6/1984 | Sato et al. | 428/156 |
| 4,465,729 A | 8/1984 | Cancio et al. | 428/167 |
| 4,543,283 A | 9/1985 | Curtze et al. | 428/38 |
| 4,554,324 A | 11/1985 | Husman et al. | 525/301 |
| 4,569,960 A | 2/1986 | Blake | 524/145 |
| 4,595,001 A | 6/1986 | Potter et al. | 128/156 |

(List continued on next page.)

FOREIGN PATENT DOCUMENTS

| | | |
|---|---|---|
| DE | 3926897 | 3/1991 |
| DE | 44 06 978 | 9/1995 |
| DE | 44 32 368 A | 3/1996 |
| DE | 19522792 | 3/1996 |
| DE | 196 28 999 | 3/1998 |
| EP | 0 099 087 | 1/1984 |
| EP | 0 056 719 B1 | 5/1987 |
| EP | 91800 | 9/1992 |
| EP | 0 525 403 A1 | 2/1993 |
| EP | 353972 | 1/1994 |
| EP | 670 338 | 9/1995 |
| EP | 0 701 822 | 3/1996 |
| EP | 0 710 545 A1 | 5/1996 |
| EP | 853 092 | 7/1998 |
| GB | 2 155 856 | 10/1985 |
| JP | 51-89540 | 8/1976 |
| JP | 96073826 | 3/1996 |
| WO | WO92/04418 | 3/1992 |
| WO | WO93/10177 | 5/1993 |
| WO | WO95/27014 | 10/1995 |
| WO | WO97/07161 | 2/1997 |
| WO | WO97/23577 | 7/1997 |
| WO | WO98/03208 | 1/1998 |
| WO | WO98/29516 | 7/1998 |
| WO | WO99/14415 | 3/1999 |

OTHER PUBLICATIONS

Y. Yamashita, et al., *Polymer Journal*, 14, 255–260 (1982).

K. Ito et al., *Macromolecules* 13, 216–221 (1980).

Nichols, R. T. and R.M. Sowers, "Laminated Materials, Glass," *Kirk–Othmer Encyclopedia of Chemical Technology*,, 4th Ed., pp. 1059–1074, 1995.

(List continued on next page.)

*Primary Examiner*—James J. Seidleck
*Assistant Examiner*—Melanie Bissett
(74) *Attorney, Agent, or Firm*—Doreen S. L. Gwin

(57) ABSTRACT

A wet-skin adhesive includes a pressure-sensitive adhesive component that includes at least one monoethylenically unsaturated (meth)acrylic acid ester comprising an alkyl group having at least 4 carbons on average and at least one monoethylenically unsaturated reinforcing monomer; and a film-forming component that includes at least one monoethylenically unsaturated (meth)acrylic acid ester comprising an alkyl group having less than 4 carbons on average and at least one hydrophilic acidic monomer, wherein the wet-stick pressure-sensitive adhesive has an initial wet skin adhesion of at least about 0.8 N/dm. Advantageously, the wet-stick adhesive has an initial wet skin adhesion that is at least about 65% of an initial dry skin adhesion.

21 Claims, No Drawings

U.S. PATENT DOCUMENTS

| | | | |
|---|---|---|---|
| 4,598,004 A | 7/1986 | Heinecke | 428/40 |
| 4,599,274 A | 7/1986 | Ando et al. | 428/442 |
| 4,619,979 A | 10/1986 | Kotnour et al. | 526/88 |
| 4,671,913 A | 6/1987 | Gen et al. | 264/171 |
| 4,737,559 A | 4/1988 | Kellen et al. | 526/291 |
| 4,833,179 A | 5/1989 | Young et al. | 522/183 |
| 4,843,134 A | 6/1989 | Kotnour et al. | 526/318.4 |
| 4,925,725 A | 5/1990 | Endo et al. | 428/156 |
| 5,091,258 A | 2/1992 | Moran | 428/437 |
| 5,100,963 A | 3/1992 | Lin | 525/221 |
| 5,147,485 A | 9/1992 | Gajewski et al. | 156/104 |
| 5,178,933 A | 1/1993 | Yoshida et al. | 428/207 |
| 5,180,756 A | 1/1993 | Rehmer et al. | 522/35 |
| 5,190,992 A | 3/1993 | Kato et al. | 522/180 |
| 5,254,388 A | 10/1993 | Melby et al. | 428/120 |
| 5,268,049 A | 12/1993 | Marriott et al. | 156/99 |
| 5,362,801 A | 11/1994 | Amici et al. | 525/57 |
| 5,382,451 A | 1/1995 | Johnson et al. | 427/208.4 |
| 5,407,971 A | 4/1995 | Everaerts et al. | 522/35 |
| 5,425,977 A | 6/1995 | Hopfe | 428/141 |
| 5,436,283 A | 7/1995 | Okada et al. | 523/120 |
| 5,445,890 A | 8/1995 | Bayha et al. | 428/431 |
| 5,455,103 A | 10/1995 | Hoagland et al. | 428/167 |
| 5,461,103 A | 10/1995 | Bafford et al. | 524/460 |
| 5,487,412 A | 1/1996 | Matthews et al. | 138/149 |
| 5,496,603 A | 3/1996 | Riedel et al. | 428/40 |
| 5,506,279 A | 4/1996 | Babu et al. | 522/34 |
| 5,536,347 A | 7/1996 | Moran | 156/103 |
| 5,547,736 A | 8/1996 | Simon et al. | 428/143 |
| 5,595,818 A | 1/1997 | Hopfe et al. | 428/327 |
| 5,613,942 A | 3/1997 | Lucast et al. | 602/52 |
| 5,620,779 A | 4/1997 | Levy et al. | 428/167 |
| 5,631,073 A | 5/1997 | Riedel et al. | 442/364 |
| 5,637,646 A | 6/1997 | Ellis | 525/309 |
| 5,679,190 A | 10/1997 | Riedel et al. | 156/62.2 |
| 5,741,542 A | 4/1998 | Williams et al. | 427/208.4 |
| 5,750,134 A | 5/1998 | Scherrer et al. | 424/434 |
| 5,804,610 A | 9/1998 | Hamer et al. | 522/182 |
| 5,969,069 A | 10/1999 | Su et al. | 526/318.44 |
| 5,976,690 A | 11/1999 | Williams et al. | 428/345 |

OTHER PUBLICATIONS

Sung Gun Chu, Chapter 8, *Handbook of Pressure Sensitive Adhesive Technology*, Second Edition, Donatas Satas, Editor, pp. 158–203, 1989.

Derwent Abstract for JP 08 295850A.

Masters, K., *Spray Drying: An Introduction to Principles, Operational Practice, and Application,* 2nd edition, Wiley, NY 1976, pp. 74–93.

Satas, D., *The Handbook of Pressure Sensitive Adhesive Technology,* 2nd edition, Van Nostrand Reinhold, NY 1989, pp. 172–173.

ASTM Designation: D 3654M–88 (Reapproved 1993), Standard Test Method for Holding Power of Pressure Sensitive Tapes (Metric).

Fox, T.G., Bulletin of the American Physical Society (ser. 2), 12.3, J5 (1956).

Kirk–Othmer Encyclopedia of Chemical Technology, 4th edition, John Wiley & Sons, NY, vol. 6, 1993, pp 635–636.

Patent Abstracts of Japan, vol. 1995, No. 1, Feb. 28, 1995 and JP 06285978, Oct. 11, 1994 (abstract).

WET-STICK ADHESIVES

FIELD OF THE INVENTION

This invention pertains to a pressure-sensitive adhesive and more particularly to a pressure-sensitive adhesive that includes a mixture of a pressure-sensitive adhesive component and a film-forming component. Significantly, such pressure-sensitive adhesives provide bond formation useful for adhesion to skin or like delicate surfaces, even when such surfaces are wet.

BACKGROUND OF INVENTION

Pressure-sensitive adhesive articles and the like are used in a wide variety of applications where there is a need to adhere to skin, for example, medical tapes, wound or surgical dressings, athletic tapes, surgical drapes, or tapes or tabs used in adhering medical devices such as sensors, electrodes, ostomy appliances, or the like. A concern with many of these adhesive coated articles is the need to balance the objective of providing sufficiently high levels of adhesion to wet skin as well as to dry skin. Thus, pressure-sensitive adhesives that adhere to wet or moist surfaces, so-called "wet stick" adhesives.

One approach in the art to providing pressure-sensitive adhesive articles for application to wet skin has been the use of pattern coated adhesives. A discontinuous adhesive coating on a backing allows the skin to breathe, at least in the areas of the backing not coated with adhesive. This approach is disclosed in U.S. Pat. No. 4,595,001 (Potter, et al.) and U.S. Pat. No. 5,613,942 (Lucast, et al.), as well as EP 353972 (Takamoto, et al.) and EP 91800 (Potter, et al.). These documents generally teach intermittent coating of adhesives onto different backings.

(Meth)acrylate pressure-sensitive adhesives are attractive materials for many applications. (Meth)acrylates are known for their optical clarity, oxidative resistance, and inherently tacky nature. Inherently tacky (meth)acrylate pressure-sensitive adhesives (i.e., materials that require no additives such as tackifying resins) are typically formulated predominately from acrylic acid ester monomers of nontertiary alcohols. Examples of such monomers include n-butyl acrylate, 2-ethylehxyl acrylate, isooctyl acrylate, isononyl acrylate, isodecyl acrylate and dodecyl acrylate. When these (meth)acrylate monomers are polymerized, the homopolymers have a glass transition temperature (Tg) of less than 10° C. This low Tg is a necessary property in (meth)acrylate materials that exhibit tack at room temperature. Such (meth)acrylate polymers are hydrophobic in nature and, without modification, are generally unsuitable as wet stick adhesives.

A means to increase the hydrophilic character of (meth)acrylate polymers is to copolymerize the (meth)acrylate monomers with hydrophilic acidic comonomers, such as acrylic acid, methacrylic acid, beta-carboxyethyl acrylate, itaconic acid, sulfoethyl acrylate, and the like. Addition of these hydrophilic acidic comonomers in minor amounts (about 1 weight percent to about 15 weight percent) can also enhance the internal or cohesive strength of the PSA. This increased polymer reinforcement, however, can diminish the tack of the hydrophilic acidic comonomer-containing (meth)acrylate copolymer.

At higher acidic comonomer levels, (meth)acrylate copolymers can dramatically lose their tack and become highly hydrophilic. When exposed to water, the moisture helps to transform these highly acidic, low tack compositions into tacky materials that are suitable as wet-stick adhesives used in many medical applications. When the water is allowed to evaporate, however, these adhesives lose their pressure-sensitive tack. Thus, although this provides suitable wet skin adhesion in some applications, there is still a need for articles having good initial wet skin adhesion in other applications, preferably, on the order of the same article's initial dry skin adhesion.

SUMMARY OF INVENTION

Briefly, in one aspect of the present invention, a wet-stick pressure-sensitive adhesive is provided wherein the pressure-sensitive adhesive comprises:
  (a) a pressure-sensitive acrylate adhesive comprising:
    (i) at least one copolymerized monoethylenically unsaturated (meth)acrylic acid ester comprising an alkyl group having at least 4 carbons on average that, when homopolymerized, preferably has a glass transition temperature of less than about 10° C. (referred to herein as monomer A); and
    (ii) at least one copolymerized monoethylenically unsaturated reinforcing monomer that, when homopolymerized, preferably has a glass transition temperature of at least about 10° C. (referred to herein as monomer B); and
  (b) a film-forming component comprising:
    (i) at least one copolymerized monoethylenically unsaturated (meth)acrylic acid ester comprising an alkyl group having less than 4 carbons on average; and
    (ii) at least one copolymerized hydrophilic acidic monomer.

Advantageously, the pressure-sensitive adhesive in accordance with the present invention adheres to wet skin.

The acrylate copolymer for the pressure-sensitive adhesive component is preferably formulated to have a resultant $T_g$ of less than about 25° C. and more preferably, less than about 10° C. The film-forming polymer component is preferably formulated to have a resultant $T_g$ of less than about 70° C. The glass transition temperatures of the homopolymers of the monomers and the pressure-sensitive adhesive are typically accurate to within ±5° C. and are measured by differential scanning calorimetry Preferably, the wet-stick pressure-sensitive adhesive of the present invention includes a (meth)acrylic acid ester monomer of the pressure-sensitive adhesive component having the following general formula:

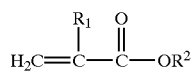

wherein $R^1$ is H or $CH_3$ and $R^2$ is a linear or branched hydrocarbon group of about 4 to about 14 carbon atoms optionally including one or more heteroatoms. More preferably, the (meth)acrylic acid ester monomer is selected from the group of n-butyl acrylate, 2-ethylhexyl acrylate, isooctyl acrylate, lauryl acrylate, and mixtures thereof. Preferably, the (meth)acrylic acid ester monomer is present in the pressure-sensitive adhesive component in an amount of about 85 wt-% to about 99 wt-%, based on the total weight of the copolymerizable monomers.

Preferably, a wet-stick adhesive of the present invention includes a hydrophilic acidic monomer that is an ethylenically unsaturated carboxylic acid, an ethylenically unsaturated sulfonic acid, an ethylenically unsaturated phosphonic acid, or mixtures thereof. More preferably, the hydrophilic acidic monomer is an ethylenically unsaturated carboxylic acid. Preferably, the hydrophilic acidic monomer is present in the film-forming component in an amount of about 1 wt-% to about 50 wt-%, based on the total weight of copolymerizable monomers.

A wet-stick pressure-sensitive adhesive of the present invention can further include an additive selected from the group consisting of a plasticizer, a tackifier, a pigment, glass beads, polymeric beads, fibers, a reinforcing agent, silica, a toughening agent, a fire retardant, an antioxidant, a stabilizer, or mixtures thereof. Additionally, the wet-stick pressure-sensitive adhesive of the present invention can be crosslinked.

Another aspect of the present invention provides an article comprising a backing and a wet-stick pressure-sensitive adhesive comprising:
(a) a pressure-sensitive adhesive component comprising:
  (i) at least one copolymerized monoethylenically unsaturated (meth)acrylic acid ester comprising an alkyl group having at least 4 carbons on average; and
  (ii) at least one copolymerized monoethylenically unsaturated reinforcing monomer; and
(b) a film-forming component comprising:
  (i) at least one copolymerized monoethylenically unsaturated (meth)acrylic acid ester comprising an alkyl group having less than 4 carbons on average; and
  (ii) at least one copolymerized hydrophilic acidic monomer.

Preferably, the article adheres to wet skin. More preferably, the article has an initial wet skin adhesion of at least about 0.8 N/dm. Additionally, an article preferably has an initial wet skin adhesion at least about 65% of an initial dry skin adhesion.

A further aspect of the present invention provides a method of making a wet-stick pressure-sensitive adhesive, the method includes combining under conditions for polymerization:
(i) at least one monoethylenically unsaturated (meth) acrylic acid ester comprising an alkyl group having at least 4 carbons on average;
(ii) at least one monoethylenically unsaturated reinforcing monomer;
(iii) at least one monoethylenically unsaturated (meth) acrylic acid ester comprising an alkyl group having less than 4 carbons on average; and
(iv) at least one hydrophilic acidic monomer, wherein at least (i) and (ii) or (iii) and (iv) are polymerized prior to combining (iii) and (iv) or (i) and (ii), respectively.

Preferably, the at least one copolymerized monoethylenically unsaturated (meth)acrylic acid ester comprising an alkyl group having less than 4 carbons on average and the at least one copolymerized hydrophilic acidic monomer are copolymerized prior to the addition of the at least one monoethylenically unsaturated (meth)acrylic acid ester comprising an alkyl group having at least 4 carbons on average and at least one copolymerized monoethylenically unsaturated reinforcing monomer.

Yet another aspect of the present invention provides a method of using an adhesive article, the method includes providing an adhesive article comprising a backing and a wet-stick pressure-sensitive adhesive layer disposed on at least one surface of the backing and adhering the adhesive article to skin. Preferably, the wet-stick pressure-sensitive adhesive includes:
(a) a pressure-sensitive adhesive component comprising:
  (i) at least one copolymerized monoethylenically unsaturated (meth)acrylic acid ester comprising an alkyl group having at least 4 carbons on average; and
  (ii) at least one copolymerized monoethylenically unsaturated reinforcing monomer; and
(b) a film-forming component comprising:
  (i) at least one copolymerized monoethylenically unsaturated (meth)acrylic acid ester comprising an alkyl group having less than 4 carbons on average; and
  (ii) at least one copolymerized hydrophilic acidic monomer.

As used herein in this application:

"pressure-sensitive adhesive" or "PSA" refers to a viscoelastic material that displays aggressive tackiness and adheres well to a wide variety of substrates after applying only light pressure (e.g., finger pressure). An acceptable quantitative description of a pressure-sensitive adhesive is given by the Dahlquist criterion, which indicates that materials having a storage modulus (G') of less than about $4.0 \times 10^5$ Pascals (measured at room temperature) have pressure-sensitive adhesive properties;

"wet-stick adhesive" refers to a material that exhibits pressure-sensitive adhesive properties when adhered to at least a wet surface, preferably to both wet and dry surfaces, particularly skin;

"(meth)acrylate monomers" are acrylic acid esters or methacrylic acid esters of nontertiary alcohols;

"hydrophilic acidic monomers" are water soluble ethylenically unsaturated, free radically reactive monomers having carboxylic acid, sulfonic acid, or phosphonic acid functionality, may be the free acid or in a partially or fully neutralized state, and are copolymerizable with the (meth)acrylate monomers;

"copolymer" includes a polymer of two or more types of polymerizable monomers, and therefore includes terpolymers, tetrapolymers, etc., which can include random copolymers, block copolymers, or sequential copolymers.

DESCRIPTION OF PREFERRED EMBODIMENT(S)

Generally, the wet stick pressure-sensitive adhesive is provided wherein the pressure-sensitive adhesive comprises:
(a) a pressure-sensitive acrylate adhesive comprising:
  (i) at least one copolymerized monoethylenically unsaturated (meth)acrylic acid ester comprising an alkyl group having at least 4 carbons on average that, when homopolymerized, preferably has a glass transition temperature of less than about 10° C. (referred to herein as monomer A); and
  (ii) at least one copolymerized monoethylenically unsaturated reinforcing monomer that, when homopolymerized, preferably has a glass transition temperature of at least about 10° C. (referred to herein as monomer B); and
(b) a film-forming component comprising:
  (i) at least one copolymerized monoethylenically unsaturated (meth)acrylic acid ester comprising an alkyl group having less than 4 carbons on average (referred to herein as monomer C); and
  (ii) at least one copolymerized hydrophilic acidic monomer either the free acid or in a partially or fully neutralized state (referred to herein as monomer D). Preferably, the pressure-sensitive adhesive in accordance with the present invention adheres to wet skin.

The present invention also provides articles that include a backing substrate having a continuous or discontinuous adhesive layer thereon. Preferably, such articles have an initial wet skin adhesion of at least about 20 g/2.5 cm (0.8 N/dm, Newtons per decimeter), and more preferably, at least about 40 g/2.5 cm (1.6 N/dm). Preferably, such articles have an initial dry skin adhesion of at least about 20 g/2.5 cm (0.8 N/dm), and more preferably, at least about 40 g/2.5 cm (1.6 N/dm). Preferably, the adhesive article (i.e., a substrate with a continuous or discontinuous layer of adhesive disposed thereon) has an initial wet skin adhesion that is at least about 65%, more preferably, at least about 75%, and most preferably, at least about 100%, of the initial dry skin adhesion. The comparison of wet to dry skin adhesion can be carried out using the test protocol described in the Examples Section. Herein, wet skin has visually observable water thereon.

(Meth)acrylate Monomer A for Pressure-sensitive Adhesive Component

Monomer A is a monoethylenically unsaturated (meth) acrylic acid ester (i.e., an alkyl acrylate or methacrylate), wherein the alkyl group has at least 4 carbon atoms (on average). Preferably, the alkyl group of the (meth)acrylate has about 4 to about 14 carbon atoms (on average). The alkyl group can optionally contain heteroatoms and can be linear or branched. When homopolymerized, these monomers yield inherently tacky polymers with glass transition temperatures which are typically less than about 10° C. Preferred such (meth)acrylate monomers have the following general formula:

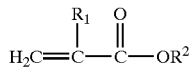

wherein $R^1$ is H or $CH_3$, the latter corresponding to where the (meth)acrylate monomer is a methacrylate monomer, and $R^2$ is broadly selected from linear or branched hydrocarbon groups and optionally including one or more heteroatoms. The number of carbon atoms in the $R^2$ group is preferably about 4 to about 14, and more preferably about 4 to about 8.

Examples of monomer A include, but are not limited to, 2-methylbutyl acrylate, isooctyl acrylate, isooctyl methacrylate, lauryl acrylate, 4-methyl-2-pentyl acrylate, isoamyl acrylate, sec-butyl acrylate, n-butyl acrylate, n-hexyl acrylate, 2-ethylhexyl acrylate, 2-ethylhexyl methacrylate, n-ocytl acrylate, n-octyl methacrylate, 2-methoxy-ethyl acrylate, 2-ethoxy-ethyl acrylate, n-decyl acrylate, isodecyl acrylate, isodecyl methacrylate, and isononyl acrylate. Preferred (meth)acrylates that can be used as monomer A include isooctyl acrylate, 2-ethyl hexyl acrylate, 2-methylbutyl acrylate, and n-butyl acrylate. Combinations of various monomers categorized as an A monomer can be used to make the pressure-sensitive adhesive component of the mixture of the present invention.

Preferably, the copolymerizable mixture of the pressure-sensitive adhesive component of the wet-stick adhesive present invention includes, based upon the total weight of the copolymerizable monomers in the pressure-sensitive adhesive component, at least about 85 weight percent (wt-%), more preferably, at least about 90 wt-%, and most preferably, at least about 95 wt-%, of monomer A. Preferably, the copolymerizable mixture of the present invention includes, based upon the total weight of the copolymerizable monomers of the pressure-sensitive adhesive component, no greater than about 99 wt-%, more preferably, no greater than about 98 wt-%, and most preferably, no greater than about 96 wt-%, of monomer A.

Reinforcing Monomer B for Pressure-sensitive Adhesive Component

Monomer B, which is a monoethylenically unsaturated reinforcing monomer, increases the glass transition temperature of the copolymer. As used here, "reinforcing" monomers are those that increase the modulus of the adhesive, and thereby its strength. Preferably, monomer B has a homopolymer $T_g$ of at least about 10° C. More preferably, monomer B is a reinforcing monoethylenically unsaturated free-radically copolymerizable (meth)acrylic monomer, including an acrylic acid, a methacrylic acid, an acrylamide, and an acrylate. Examples of monomer B include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer B include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Preferred reinforcing monofunctional acrylic monomers that can be used as monomers B include acrylic acid and methacrylic acid. Combinations of various reinforcing monofunctional monomers categorized as a B monomer can be used to make the copolymer for the pressure-sensitive adhesive component used in making the mixture of the present invention.

Preferably, the copolymerizable mixture of the pressure-sensitive adhesive component of the wet-stick adhesive of the present invention includes, based upon the total weight of the copolymerizable monomers of the pressure-sensitive adhesive component, at least about 1 wt-%, more preferably, at least about 2 wt-%, and most preferably, at least about 6 wt-% by weight of monomer B. Preferably, the copolymerizable mixture of the present invention includes, based upon the total weight of the copolymerizable monomers, no greater than about 15 wt-%, more preferably, no greater than about 10 wt-%, and most preferably, no greater than about 5 wt-%, of monomer B.

(Meth)acrylate Monomer C for Film-forming Component

Monomer C is a monoethylenically unsaturated (meth) acrylic acid ester (i.e., an alkyl acrylate or methacrylate), wherein the alkyl group has less than 4 carbon atoms (on average). Preferably, the alkyl group of the (meth)acrylate has about 1 to about 2 carbon atoms (on average). When homopolymerized, these monomers yield essentially non-tacky polymers with a Tg of no greater than about 120° C. Preferred (meth)acrylate monomers have the following general formula:

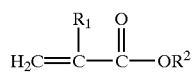

wherein $R^1$ is H or $CH_3$, and $R^2$ is broadly selected from linear or branched hydrocarbon groups and optionally including one or more heteroatoms. The number of carbon atoms in the $R^2$ group is preferably 1 or 2.

Examples of monomer C include, but are not limited to, methyl acrylate, methyl methacrylate, ethyl acrylate, propyl acrylate, and propyl methacrylate. Preferred (meth)acrylates that can be used as monomer C include, ethyl acrylate and methyl methacrylate. Combinations of various monomers categorized as a C monomer can be used to make the film-forming component of the mixture of the present invention.

Preferably, the copolymerizable mixture of the film-forming component of the wet-stick adhesive of the present invention includes, based upon the total weight of the copolymerizable monomers of the film-forming component, at least about 50 weight percent (wt-%), more preferably, at least about 75 wt-%, and most preferably, at least about 85 wt-%, of monomer C. Preferably, the copolymerizable mixture in the wet-stick adhesive of the present invention includes, based upon the total weight of the copolymerizable monomers of the film-forming component, no greater than about 99 wt-%, more preferably, no greater than about 95 wt-%, of monomer C.

Hydrophilic Acidic Monomer D for Film-forming Component

Useful copolymerized hydrophilic acidic monomers for use in either the pressure-sensitive adhesive component or the film-forming component of the wet-stick adhesive of the present invention include, but are not limited to, those selected from ethylenically unsaturated carboxylic acids, ethylenically unsaturated sulfonic acids, ethylenically unsaturated phosphonic acids, and mixtures thereof. The acidic comonomer may be present as the free acid, or in a fully or partially neutralized form. Suitable neutralizing agents include metal hydroxides (e.g. NaOH), quaternary amines, etc. Examples of such compounds include, but are not limited to, acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phopshonic acid, and the like. Various combinations of these monomers can be used if desired. Due to their availability and effectiveness in reinforcing (meth)acrylate pressure-sensitive adhesives, particularly preferred hydrophilic acidic monomers are the ethylenically unsaturated carboxylic acids, most preferably acrylic acid. Because monomer D is a subset of monomer B, both components can have the same second monomer present.

Preferably, the copolymerizable mixture of the film-forming component of the wet stick adhesive of the present invention includes, based upon the total weight of the copolymerizable monomers of the film-forming component, at least about 1 wt-%, more preferably, at least about 5 wt-% by weight of monomer D. Preferably, the copolymerizable mixture of the present invention includes, based upon the total weight of the copolymerizable monomers in the film-forming component, no greater than about 50 wt-%, more preferably, no greater than about 25 wt-%, and most preferably, no greater than about 15 wt-%, of monomer D.

Optional Monomers

Minor amounts of monomers copolymerizable with the monomers of either component of the wet stick adhesive of the present invention, such as vinyl ester, and N-vinyl lactams, can be used. Examples include, but are not limited to, polystyrene macromer, poly(methyl methacrylate) macromer, poly (methoxy-ethylene glycol) macrometer,4-(N,N-dimethylamido)butylacrylate; N-vinyl lactams, such as, N-vinyl pyrrolidone, N-vinyl caprolactam; and N-vinyl formamide. Various combinations of these monomers can be used if desired. Preferably, an optional monomer can be included in either of the components of the wet-stick adhesive of the present invention in an amount of about 2% by weight to about 20% by weight of the component.

Crosslinkers

In order to improve shear or cohesive strength, control elastic modulus, and preadhesion tack, for example, of the adhesive of the present invention, the copolymer formed from the monomers of the pressure-sensitive adhesive component as well as those in the film-forming component can be crosslinked. Preferably, the crosslinking agent is one that is copolymerized with monomers A and B and/or monomers C and D. The crosslinking agent may produce chemical crosslinks (e.g., covalent bonds). Alternatively, it may produce physical crosslinks that result, for example, from the formation of reinforcing domains due to phase separation or acid base interactions. Suitable crosslinking agents are disclosed in U.S. Pat. Nos. 4,379,201 (Heilman), 4,737,559 (Kellen), 5,506,279 (Babu et al.), and 4,554,324 (Husman). Combinations of various crosslinking agents can be used to make the copolymers components used the present invention. It should be understood, however, that such crosslinking agents are optional.

Such crosslinking agents include thermal crosslinking agents such as a multifunctional aziridine, for example. One example is 1,1'-(1,3-phenylene dicarbonyl)-bis-(2-methylaziridine), often referred to as "bisamide." Such chemical crosslinkers can be added into solvent-based adhesives containing acid functionality after polymerization and activated by heat during oven drying of the coated adhesive.

Another class of crosslinking agents are the copolymerizable monoethylenically unsaturated aromatic ketone monomers free of ortho-aromatic hydroxyl groups such as those disclosed in U.S. Pat. No. 4,737,559 (Kellen). Specific examples include para-acryloxybenzophenone, para-acryloxyethoxybenzophenone, para-N-(methylacryloxyethyl)carbamoylethoxybenzophenone, para-acryloxyacetophenone, ortho-acrylamidoacetophenone, acrylated anthraquinones, and the like. Other suitable crosslinking agents include chemical crosslinkers that rely upon free radicals to carry out the crosslinking reaction. Reagents such as peroxides, for example, serve as a precursor of free radicals. When heated sufficiently, these precursors will generate free radicals that bring about a crosslinking reaction of the polymer chains.

Aside from thermal or photosensitive crosslinkers, crosslinking may also be achieved using high energy electromagnetic radiation such as gamma or e-beam radiation, for example.

A physical crosslinking agent may also be used. In one embodiment, the physical crosslinking agent is a high Tg macrometer such as those that include vinyl functionality and are based upon polystyrene and polymethylmethacrylate. Such vinyl-terminated polymeric crosslinking monomers are sometimes referred to as macromolecular monomers (i.e., "macromers"). Such monomers are known and may be prepared by the methods disclosed in U.S. Pat. Nos. 3,786,116 (Milkovich et al.) and 3,842,059 (Milkovich et al.), as well as Y. Yamashita et al., *Polymer Journal*, 14, 255–260 (1982), and K. Ito et al., *Macromolecules*, 13, 216–221 (1980). Typically, such monomers are prepared by anionic polymerization or free radical polymerization.

Metal cross-linkers are useful also. Examples include metal-containing salts or other metal-containing compounds. Suitable metals include zinc, titanium, for example. Examples of metal-containing compounds include zinc oxide, zinc ammonium carbonates, zinc stearate, etc.

If used, the crosslinking agent is used in an effective amount, by which is meant an amount that is sufficient to cause crosslinking of the pressure-sensitive adhesive to provide adequate cohesive strength to produce the desired final adhesion properties to the substrate of interest. Preferably, if used, the crosslinking agent is used in an amount of about 0.1 part to about 10 parts, based on 100 parts of monomers.

Other Additives

Other additives can be included in the polymerizable mixtures for the pressure-sensitive adhesive component and the film-forming component, or added at the time of compounding or coating of the mixture of these two components to change the properties of the adhesive. Such additives, or fillers, include plasticizers, tackifiers, pigments, glass or polymeric bubbles or beads (which may be expanded or unexpanded), fibers, reinforcing agents, hydrophobic or hydrophilic silica, toughening agents, fire retardants, antioxidants, finely ground polymer particles such as polyesters, nylon, and polypropylene, and stabilizers. The additives are added in amounts sufficient to obtain the desired end-use properties.

If included, plasticizers are selected for use in the wet stick adhesive such that they improve the pressure-sensitive adhesive characteristics of the wet stick adhesive of the present invention. Preferably, a plasticizer is compatible with the copolymers, and are nonvolatile. Generally, any significant bleeding or migration from the composition could result in loss of wet-stick adhesion properties.

Particularly useful plasticizing agents include polyalkylene oxides such as polyethylene oxides, polypropylene oxides, polyethylene glycols; alkyl or aryl functionalized polyalkylene oxides, such as that commercially available under the trade designation PYCAL 94 (a phenyl ether of polyethylene oxide, from ICI Chemicals); benzoyl functionalized polyethers, commercially available under the trade designation BENZOFLEX 400 (polypropylene glycol dibenzoate, from Velsicol Chemicals) and monomethyl ethers of polyethylene oxides, and mixtures thereof. Other useful agents include polyalkylene oxide block copolymer plasticizers such as those commercially available under the trade designations PLURONIC, TETRONIC, both from BASF, Mount Olive, N.J. The plasticizing agent can be used in amounts of from about 2 to 50 pph (parts by weight per 100 parts of the (meth)acrylate and hydrophilic acidic comonomers). Typically, the plasticizing agent is present in the adhesive in amounts from about 5 to 25 pph. The amount of plasticizer required depends upon the type and ratios of the (meth)acrylate and hydrophilic acidic comonomers employed in the polymerizable mixture and the chemical class and molecular weight of the plasticizing agent used in the composition. Suitable tackifiers are described in International Publication No. WO 97/23577 (Hyde et al.) and include those such as rosin esters, such as that commercially available under the trade designation FORAL 85, from Hercules, Inc., aromatic resins, such as that commercially available under the trade designation PICCOTEX LC-55wk, aliphatic resins, such as that commercially available under the trade designation PICCOTAC 95, both from Hercules, Inc., terpene resins, such as α-pinene and β-pinene, each commercially available under the trade designations PICCOLYTE A-115 and ZONAREZ B-100, respectively, both from Arizona Chemical Co., and hydrocarbon resins, such as that commercially available under the trade designation ECR-180 from Exxon Chemical Co.

Polymerization Initiators

A free radical initiator is preferably added to aid in the copolymerization of (meth)acrylate and acidic comonomers. The type of initiator used depends on the polymerization process. Photoinitiators which are useful for polymerizing the polymerizable mixture of monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1, 1-propanedione-2-(O-ethoxycarbonyl) oxime. An example of a commercially available photoinitiator is IRGACURE 651 (2,2-dimethoxy-1,2-diphenylethane-1-one, commercially available from Ciba-Geigy Corporation,). Examples of suitable thermal initiators include AIBN (2,2'-azobis(isobutyronitrile), hydroperoxides, such as tert-butyl hydroperoxide, and peroxides, such as benzoyl peroxide and cyclohexane peroxide. Generally, the initiator is present in an amount of about 0.005 weight percent to about 1 weight percent based on the weight of the copolymerizable monomers.

Polymerization Chain Transfer Agents

Optionally, the composition also includes a chain transfer agent to control the molecular weight of the polymerized compositions. Chain transfer agents are materials that regulate free radical polymerization and are generally known in the art. Suitable chain transfer agents include alcohols (e.g., methanol, ethanol and isopropanol), halogenated hydrocarbons such as carbon tetrabromide; sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether and mixtures thereof. The amount of chain transfer agent that is useful depends upon the desired molecular weight and the type of chain transfer agent. A non-alcohol chain transfer agent is typically used in amounts from about 0.001 part to about 10 parts by weight per 100 parts of total monomer, and preferably from about 0.01 part to about 0.5 part, and most preferably from about 0.02 part to about 0.20 part, and can be higher for alcohol-containing systems.

Methods and Making Adhesive Compositions

Each of the adhesive components (i.e., the pressure-sensitive adhesive and the film-forming components) in the wet-stick adhesive of the present invention can be polymerized by a wide variety of conventional free radical polymerization methods. Suitable methods include those described in U.S. Pat. Nos. 4,181,752 (Martens, et al.); 4,833,179 (Young et al.); 5,804,610 (Hamer et al.); and 5,382,451 (Johnson, et al.).

For example, in a solution polymerization method, the alkyl (meth)acrylate monomers acidic monomers, along with a suitable inert organic solvent, and free radically copolymerizable crosslinker, if used, are charged into a four-neck reaction vessel which is equipped with a stirrer, a thermometer, a condenser, an addition funnel, and a thermowatch. After this monomer mixture is charged into the reaction vessel, a concentrated thermal free radical initiator solution is added to the addition funnel. The whole reaction vessel and addition funnel and their contents are then purged with nitrogen to create an inert atmosphere. Once purged, the solution within the vessel is heated to decompose the added thermal initiator, and the mixture is stirred during the course of the reaction. A conversion of about 98 percent to about 99 percent is typically obtained in about 20 hours. If desired, solvent can be removed to yield a hot melt coatable adhesive. Suitable inert organic solvents, if required, may be any organic liquid which is inert to the reactants and product and will not otherwise adversely affect the reaction. Such solvents include ethyl acetate, acetone, methyl ethyl ketones, and mixtures thereof. The amount of solvent is generally about 30 percent by weight to about 80 percent by weight based on the total weight of the reactants (monomer, crosslinker, initiator) and solvent.

Another polymerization method is the ultraviolet (UV) radiation initiated photopolymerization of the monomer mixture. This composition, along with suitable photoinitiator and crosslinker, is coated onto a flexible carrier web and polymerized in an inert, i.e., oxygen-free, atmosphere, such as a nitrogen atmosphere, for example. A sufficiently inert atmosphere can be achieved by covering a layer of the photoactive coating with a plastic film that is substantially transparent to ultraviolet radiation, and irradiating through that film in air using fluorescent-type ultraviolet lamps that generally give a total radiation dose of about 500 milliJoules/cm$^2$.

Solventless polymerization methods, such as the continuous free radical polymerization in an extruder described in U.S. Pat. Nos. 4,619,979 (Kotnour, et al.) and 4,843,134 (Kotnour, et al.); the essentially adiabatic polymerization methods using a batch reactor disclosed in U.S. Pat. No. 5,637,646 (Ellis); and, the methods described for polymerizing packaged pre-adhesive compositions described in U.S. Pat. No. 5,804,610 (Hamer, et al.) may also be utilized to prepare the polymers.

An adhesive composition according to the present invention can be formed by mixing the PSA component and film forming component or monomer(s) C and/or D can be present during polymerization of monomers A and B. Alternatively, monomer(s) A and/or B can be present during the polymerization of monomers C and D.

The adhesive compositions of the present invention may be applied to a backing by a variety of coating methods including brush, roll, spray, speed, wire, gravure, transfer roll, air knife, doctor blade coating, or by hot melt coating, with the latter being preferred.

If the composition includes a solvent or water, it is then dried at a temperature (e.g., about 65° C. to about 120° C.) and a time (e.g., several minutes to about one hour) so as to provide an adhesive tape, for example. The thickness of the layer of adhesive may vary over a broad range of about 10 microns to several hundred microns (e.g., about 200 microns).

Once the adhesive composition has been coated, and optionally crosslinked, the adhesive surface of the article may, optionally, be protected with a temporary, removable release liner (i.e., protective liner) such as polyolefin (e.g., polyethylene or polypropylene) or polyester (e.g., polyethylene terephthalate) film, or a plastic film. Such films may be treated with a release material such as silicones, waxes, fluorocarbons, and the like.

Backing and Articles

The wet stick pressure-sensitive adhesives of the present invention that adhere to wet or moist skin and similar surfaces are useful in many medical applications. For example, these wet stick adhesives are useful in medical applications, such as surgical tapes, bandages, athletic tapes, wound dressings, and drapes to adhere to moist skin surfaces such as wound or areas of the body prone to moistness. The wet-stick adhesive can be coated onto any backing suitable for medical uses including occlusive (substantially non-breathable) and non-occlusive (breathable) backings. Occlusive backings are also known as low porosity backings. Non-limiting examples of occlusive backings include films, foams, and laminates thereof. Non-limiting examples of non-occlusive backings include woven substrates, non-woven substrates (such as hydroentangled materials), melt blown webs, foams, and thermally embossed nonwoven substrates, such as those described in U.S. Pat. No. 5,496,603 (Riedel, et al.)

Typically, the wet-stick adhesive is in the form of a continuous or discontinuous coating on at least one major surface of a backing. The backing may include one or more layers. Examples of suitable backings include materials with a relatively low content of hydrophilic components such as polyester (e.g., commercially available under the designation HYTREL, such as HYTREL 4056, from DuPont Co.), polyurethane (e.g., commercially available under the designation ESTANE, such as ESTANE 58309, from B. F. Goodrich Co.), polyether block amine (e.g., commercially available under the designation PEBAX, such as PEBAX 2533 and 3533, from Atochem Co.), and porous polyethylene resins. Also suitable are materials having a relatively high content of hydrophilic components (and thus high moisture vapor transmission properties). Examples include certain polyether amides such as PEBAX 4011RN00 (Atochem Co.), and polyurethanes described in U.S. Pat. No. 4,598,004 (Heinecke). Both classes of materials may also be used in combination with each other (e.g., in sandwich-type arrangements) to tailor the moisture vapor transmission properties of the dressing.

EXAMPLES

This invention is further illustrated by the following examples that are not intended to limit the scope of the invention. In the examples, all parts, ratios and percentages are by weight unless otherwise indicated. The following test methods were used to evaluate and characterize the wet stick adhesive compositions produced in the examples. All materials are commercially available, for example from Aldrich Chemicals (Milwaukee, Wis.), unless otherwise indicated or described.

TEST PROTOCOLS

Evaluation of the tape performance of a composition to human skin is an inherently temperamental determination. Human skin possesses wide variations in composition, topography, and the presence/absence of various body fluids. However, comparative average values of tape properties are attainable by using test results from several individuals as described herein.

Adhesion to Dry and Wet Skin

Initial skin adhesion ($T_0$) and adhesion after varying dwell times ($T_{24}$,$T_{48}$) was measured to wet and dry skin in accordance with the widely accepted PSTC-1 Peel Adhesion Test (incorporated herein by reference), a testing protocol established by the Specifications and Technical Committee of the Pressure-sensitive Tape Council located at 5700 Old Orchard Road, Skokie, Ill. The test was modified for our purposes by applying the tape to the skin of a living human.

For dry skin adhesion testing, two samples (one for $T_0$ and one for $T_{24}$ or $T_{48}$), each measuring 2.5-cm wide by 7.6-cm long, were applied to the back of each of six human subjects. The subjects were placed in a prone position with arms at their sides and heads turned to one side. Samples were applied without tension or pulling of skin to both sides of the spinal column with the length of each sample positioned at a right angle to the spinal column.

For initial ($T_0$) wet skin adhesion testing, samples were applied in the manner described above to skin which had been sprayed with a measured amount of water (about 20 µL), so that the skin was visibly wet, immediately before application of the sample.

The samples were pressed into place with a 2-kg roller moved at a rate of approximately 2.5 cm/sec with a single forward and reverse pass. No manual pressure was applied to the roller during application.

The samples were then removed five minutes ($T_0$ wet or dry), or 24 or 48±2 hours ($T_{24}/T_{48}$) after application at a removal angle of 180° and a removal rate of 15 cm/min using a conventional adhesion tester equipped with a 11.3 kg test line attached to a 2.5 cm clip. The clip was attached to the edge of the sample furthest from the spinal column by manually lifting about 1 cm of the sample from the skin and attaching the clip to the raised edge. The adhesion test was a strain-gauge mounted on a motor-driven carriage.

The measured force required to effect removal of each tape sample was reported (as an average of 6 sample replications) in Newtons (N) per dm. Preferably, initial adhesion to wet or dry skin is at least 0.8 N/dm. The ratio of wet to dry initial adhesion is preferably at least 0.65.

Tape Gentleness

The example tapes were tested using a clinical method which evaluates the effect on the skin of repeated applications of the samples tapes on a human subject. Tape samples are applied to human subjects' backs in the manner described above for the dry skin adhesion testing, and then removed by hand 25±2 hours later. The clinical researcher then does a visual assessment of the condition of the area under the tapes, and if the condition is acceptable, a new piece of tape is applied to the same spot, then removed by hand after another 25±2 hours. This sequence is repeated for a maximum of 8 tape applications, after which the test is discontinued. The visual assessment of skin condition involves a rating on a scale from "0" being none to "5" being extensive, based on the amount of erythema and edema (redness and swelling) and denudation (skin stripping) of the test site. If the clinical rates a site with a 2.0 greater, the skin condition is considered unacceptable and no further tape samples are applied.

The gentleness data are expressed as a numeric value, which is the difference between the number of applications of a test tape as compared to the number of applications of the nonwoven backing tape commercially available under the trade designation MICROPORE, from 3M Company, St. Paul, Minn., tested in the same experiment (i.e. on the same human subjects for the same duration). For example, if the average number of applications (from 6–10 test subjects) of MICROPORE tape is 8.00, and a sample has an average of 7.17, the sample receives a score of 0.83. The scores are then assigned a gentleness description based on the following scale:

| Score | Rating |
|---|---|
| 0.00–1.00 | very gentle |
| 1.00–2.00 | gentle |
| 2.00–3.25 | moderately gentle |
| 3.25–4.50 | moderately traumatic |
| 4.50–5.50 | traumatic |
| 5.50–6.50 | very traumatic |

Porosity

Porosity was evaluated by a procedure wherein the time (in seconds) necessary for an inner cylinder of a Gurley densometer to force 100 cc of air through a 25-mm circular sample of the sample is determined in a manner analogous to that described in ASTM D737-75. Samples with Gurley porosity values of >100 sec are considered occlusive.

Moisture Vapor Transmission Rate (MVTR)

MVTR was evaluated in a manner analogous to that described in ASTM E 96-80 at 40° C. and expressed in grams transmitted per square meter per day ($g/m^2/24$ hr). A tape sample must exhibit an MVTR value of not less than 500 $g/m^2/24$ hr to be considered permeable to water vapor.

Examples 1–11 and Comparative Examples 1–2

Preparation of Pressure-sensitive Adhesive (PSA) Mixtures and Corresponding Adhesive Tapes A series of hot-melt polyacrylate PSAs were prepared by blending an isooctyl acrylate (IOA)/methyl methacrylate (MMA) (96/4) component PSA ("PSA A", prepared as described in U.S. Pat. No. 4,833,179 (Young et al), Example 5, with a film-forming component comprised of either ethyl acrylate (EA)/acrylic acid (AA) (92/8) copolymer (AVALURE AC 210, B. F. Goodrich, Cleveland, Ohio) or MMA/EA/AA (55/33/12) terpolymer (AVALURE AC 315, B. F. Goodrich). Optionally added to the polymer mixtures were the hydrophilic plasticizer methoxy poly(ethylene glycol) (MPEG 550, Union Carbide, Danbury, Conn.) and/or one of the following tackifying resins: rosin-based FORAL 85 (Hercules Inc., Wilmington, Del.) or hydrocarbon tackifier ECR 180 (Exxon Chemical Co., Houston, Tex.). The hydrophilic polymer TETRONIC 904 (BASF, Mount Olive, N.J.) was included in the adhesive composition of Example 11. In the case of each polymer mixture, molten components were added to a twin-screw extruder (temperature maintained at less than or equal to 140° C.) equipped with a contact die coating station, blended until homogeneous, and then coated onto a nonwoven polyester/rayon backing as described in U.S. Pat. Nos. 5,631,073; 5,679,190; and 5,496,603 (all to Reidel et al.) at a coating weight of about 25.1 $g/m^2$.

The resulting adhesive tapes (Examples 1–11) were subsequently evaluated for skin adhesion, tape gentleness, MVTR, and porosity according to the test protocols described herein. The composition of the PSA polymer mixtures and the results of skin adhesion evaluations are provided in Table 1A. The results of tape gentleness, MVTR, and porosity evaluations are reported in Table 1B. Also provided in both Tables 1A and 1B are the results of testing the nonwoven backing with only a PSA A coating (Comparative Example 1) and of testing commercial MICROPORE surgical tape (Comparative Example 2), available from 3M Company, St. Paul, Minn.

All of the adhesive tapes coated with the PSA polymer mixtures of these examples 1–11 demonstrated good initial skin adhesion to wet (at least 1.67 N/dm) and dry skin (at least 1.38 N/dm), and a favorable wet/dry adhesion ratio. For each of the examples, dry and wet skin adhesion was greater than the nonwoven polyester/rayon backing coated only with PSA A (Comparative Example 1). These adhesive tape examples also demonstrated excellent breathability (based on MVTR and porosity values) that was significantly improved over Comparative Example 1. The examples ranged from very gentle to moderately gentle based on the tape gentleness test.

TABLE 1A

PSA Polymer Mixtures and Corresponding Adhesive Tapes
(Polyester/Rayon Backing) Skin Adhesion Results

| | PSA Polymer Mixtures | | Tapes: Skin Adhesion (N/dm) | | | |
|---|---|---|---|---|---|---|
| Ex. | Components | Composition | $T_0$ (Dry) | $T_0$ (Wet) | $T_0$ (Wet)/ $T_0$ (Dry) | $T_{24}$ (Dry) |
| 1 | PSA A/AC 210 | 80/20 | 2.22 | 2.99 | 1.35 | 8.88 |
| 2 | PSA A/AC 210/MPEG | 75/20/5 | 2.19 | 2.80 | 1.28 | 8.62 |
| 3 | PSA A/AC 210/MPEG | 80/10/10 | 1.67 | 2.29 | 1.37 | 8.23 |
| 4 | PSA A/AC 210/MPEG | 90/5/5 | 1.57 | 1.67 | 1.06 | 7.14 |
| 5 | PSA A/AC 210/MPEG/ECR 180 | 70/14/8/8 | 2.12 | 2.51 | 1.18 | 10.42 |
| 6 | PSA A/AC 210/MPEG/FORAL 85 | 70/14/8/8 | 2.15 | 3.06 | 1.42 | 9.26 |
| 7 | PSA A/AC 315/ECR 180 | 70/15/15 | 1.38 | 2.19 | 1.59 | 6.82 |
| 8 | PSA A/AC 315/FORAL 85 | 70/15/15 | 2.29 | 2.64 | 1.15 | 7.14 |
| 9 | PSA A/AC 315/MPEG/ECR 180 | 70/8/8/14 | 1.87 | 1.87 | 1.00 | 6.37 |
| 10 | PSA A/AC 315/MPEG/FORAL 85 | 70/8/8/14 | 2.06 | 2.48 | 1.20 | 6.50 |
| 11 | PSA A/AC 315/TETRONIC 904 | 80/10/10 | 1.67 | 1.77 | 1.06 | 7.71 |
| C1 | PSA A | 100 | 1.29 | 1.22 | 0.95 | 7.33 |
| C2 | MICROPORE Surgical Tape | | 0.88 | 2.50 | 2.84 | 4.13 |

TABLE 1B

PSA Polymer Mixtures and Corresponding Adhesive Tapes
(Polyester/Rayon Backing)
Tape Gentleness, MVTR, and Porosity Results

| | PSA Polymer Mixtures | | Adhesive Tapes | | |
|---|---|---|---|---|---|
| Ex. | Components | Comp. | Tape Gentleness | MVTR ($g/m^2/24$ hr) | Porosity (Sec.) |
| 1 | PSA A/AC 210 | 80/20 | 1.17 | 2796 | 23.0 |
| 2 | PSA A/AC 210/MPEG | 75/20/5 | 0.50 | 3468 | 18.2 |
| 3 | PSA A/AC 210/MPEG | 80/10/10 | 0.17 | 4210 | 4.4 |
| 4 | PSA A/AC 210/MPEG | 90/5/5 | 0.67 | 1169 | 118.7 |
| 5 | PSA A/AC 210/MPEG/ECR 180 | 70/14/8/8 | 0.00 | 2093 | 14.0 |
| 6 | PSA A/AC 210/MPEG/FORAL 85 | 70/14/8/8 | 0.00 | 2923 | 4.4 |
| 7 | PSA A/AC 315/ECR 180 | 70/15/15 | 2.17 | 1034 | 20.1 |
| 8 | PSA A/AC 315/FORAL 85 | 70/15/15 | 3.17 | 1982 | 23.0 |
| 9 | PSA A/AC 315/MPEG/ECR 180 | 70/8/8/14 | 1.50 | 1469 | 98.0 |
| 10 | PSA A/AC 315/MPEG/FORAL 85 | 70/8/8/14 | 3.17 | 2109 | 14.1 |
| 11 | PSA A/AC 315/TETRONIC 904 | 80/10/10 | 0.40 | 1093 | 55.5 |
| C1 | PSA A | 100 | 0.50 | 464 | 174.0 |
| C2 | MICROPORE Surgical Tape | | 0.00 | 5269 | 2.2 |

Examples 12–29 and Comparative Example 3

Preparation of PSA Mixtures and Corresponding Adhesive Tapes

A series of hot-melt polyacrylate PSA polymer mixtures and corresponding adhesive tapes were prepared as described in Examples 1–11, except that an IOA/AA (96/4) copolymer PSA ("PSA B") prepared with 0.05% ABP photoinitiator (para-acryloxybenzophenone, described in U.S. Pat. No. 4,737,559 (Kellen et al.)) as generally described in Example 1 of U.S. Pat. No. 5,804,610, was substituted for "PSA A". In the case of each polymer mixture, molten components were added to a twin-screw extruder (temperature maintained at less or equal to 140° C.) equipped with a contact die coating station, blended until homogenous, and then coated onto a nonwoven polyester/rayon backing as described in U.S. Pat. Nos. 5,631,073; 5,679,190; and 5,496,603 (all to Riedel et al.) at a coating weight of about 25.1 g/m². Several days after coating, the adhesive tape samples were UV cured at 700 ml of UV-A/cm². No attempt was made in these examples to optimize the post-coating curing conditions.

The resulting adhesive tapes (Examples 12–29) were subsequently evaluated for skin adhesion, tape gentleness, MVTR, and porosity according to the test protocols described herein. The composition of the PSA polymer mixture and the results of skin adhesion evaluations are provided in Table 2A. The results of tape gentleness, MVTR, and porosity evaluations are reported in Table 2B. Also provided in both Tables 2A and 2B are the results of testing the commercial MICROPORE surgical tape (Comparative Example 3.

Observations $T_0$ wet and dry are above 1.35 N/dm, and nearly all of the wet/dry initial adhesion ratios were >0.8. All samples are highly breathable as seen by MVTR and porosity, and nearly all are rated gentle or very gentle.

TABLE 2A

PSA Polymer Mixtures and Corresponding Adhesive Tapes
(Polyester/Rayon Backing) Skin Adhesion Results

| | PSA Polymer Mixtures | | Tapes: Skin Adhesion (N/dm) | | | |
|---|---|---|---|---|---|---|
| Ex. | Components | Composition | $T_0$ (Dry) | $T_0$ (Wet) | $T_0$ (Wet) / $T_0$ (Dry) | $T_{24}$ (Dry) |
| 12 | PSA B/AC 210 | 80/20 | 1.71 | 2.22 | 1.30 | 6.88 |
| 13 | PSA B/AC 210/MPEG | 90/5/5 | 2.06 | 2.86 | 1.39 | 8.88 |
| 14 | PSA B/AC 210/MPEG | 75/20/5 | 1.96 | 2.41 | 1.23 | 7.53 |
| 15 | PSA B/AC 210/MPEG | 80/10/10 | 3.09 | 2.64 | 0.85 | 8.30 |
| 16 | PSA B/AC 210/MPEG/ECR 180 | 70/8/8/14 | 7.01 | 4.73 | 0.67 | 10.23 |
| 17 | PSA B/AC 210/MPEG/FORAL 85 | 70/8/8/14 | 9.39 | 5.60 | 0.60 | 10.42 |
| 18 | PSA B/AC 315 | 90/10 | 1.29 | 1.77 | 1.37 | 4.63 |
| 19 | PSA B/AC 315/ECR 180 | 70/15/15 | 1.35 | 1.46 | 1.08 | 6.88 |
| 20 | PSA B/AC 315/ECR-180 | 70/15/15 | 1.51 | 2.07 | 1.37 | 7.87 |
| 21 | PSA B/AC 315/FORAL 85 | 70/15/15 | 2.38 | 3.08 | 1.29 | 8.20 |
| 22 | PSA B/AC 315/MPEG | 60/20/20 | | | | |
| 23 | PSA B/AC 315/MPEG | 90/5/5 | 1.83 | 2.35 | 1.28 | 7.53 |
| 24 | PSA B/AC 315/MPEG | 70/10/20 | 3.60 | 3.27 | 0.91 | 8.80 |
| 25 | PSA B/AC 315/MPEG | 80/10/10 | 1.88 | 2.61 | 1.39 | 8.38 |
| 26 | PSA B/AC 315/MPEG | 60/20/20 | 2.91 | 2.38 | 0.82 | 7.40 |
| 27 | PSA B/AC 315/MPEG/ECR 180 | 70/8/8/14 | 5.44 | 4.46 | 0.82 | 9.22 |
| 28 | PSA B/AC 315/MPEG/FORAL 85 | 70/8/8/14 | 4.20 | 4.46 | 1.06 | 5.91 |
| 29 | PSA B/AC 315/TETRONIC 904 | 80/10/10 | 2.66 | 3.36 | 1.26 | 9.65 |
| C3 | MICROPORE Surgical Tape | | 0.80 | 2.44 | 3.05 | 3.79 |

TABLE 2B

PSA Polymer Mixtures and Corresponding Adhesive Tapes
(Polyester/Rayon Backing)
Tape Gentleness, MVTR, and Porosity Results

| | PSA Polymer Mixtures | | Adhesive Tapes | | |
|---|---|---|---|---|---|
| Ex. | Components | Composition | Tape Gentleness | MVTR ($g/m^2/24$ hr) | Porosity (Sec.) |
| 12 | PSA B/AC 210 | 80/20 | 0.00 | 8044 | 1.1 |
| 13 | PSA B/AC 210/MPEG | 90/5/5 | 0.50 | 5016 | 1.1 |
| 14 | PSA B/AC 210/MPEG | 75/20/5 | 0.83 | 6702 | 0.5 |
| 15 | PSA B/AC 210/MPEG | 80/10/10 | 0.17 | 4330 | 1.1 |
| 16 | PSA B/AC 210/MPEG/ECR 180 | 70/8/8/14 | 0.67 | 4330 | 3.8 |
| 17 | PSA B/AC 210/MPEG/FORAL 85 | 70/8/8/14 | 0.83 | 3820 | 2.8 |
| 18 | PSA B/AC 315 | 90/10 | 0.67 | 3308 | 3.9 |
| 19 | PSA B/AC 315/ECR 180 | 70/15/15 | 3.33 | 1787 | 7.1 |
| 20 | PSA B/AC 315/ECR 180 | 70/15/15 | 2.20 | 3986 | 4.5 |
| 21 | PSA B/AC 315/FORAL 85 | 70/15/15 | 3.80 | 5072 | 1.9 |
| 22 | PSA B/AC 315/MPEG | 60/20/20 | | 2161 | 7.9 |
| 23 | PSA B/AC 315/MPEG | 90/5/5 | 0.83 | 4275 | 2.4 |
| 24 | PSA B/AC 315/MPEG | 70/10/20 | 0.80 | 3119 | 6.8 |
| 25 | PSA B/AC 315/MPEG | 80/10/10 | 2.00 | 2811 | 3.7 |
| 26 | PSA B/AC 315/MPEG | 60/20/20 | 0.80 | 2155 | 7.3 |
| 27 | PSA B/AC 315/MPEG/ECR 180 | 70/8/8/14 | 3.40 | 5120 | 1.2 |
| 28 | PSA B/AC 315/MPEG/FORAL 85 | 70/8/8/14 | 2.60 | 5914 | 0.9 |
| 29 | PSA B/AC 315/TETRONIC 904 | 80/10/10 | 1.00 | 5801 | 1.6 |
| C3 | MICROPORE Surgical Tape | | 0.00 | 3915 | 2.9 |

Examples 30–46 and Comparative Examples 4 and 5

Preparation of PSA Mixtures and Corresponding Adhesive Tapes

A series of hot-melt polyacrylate PSA polymer mixtures and corresponding adhesives tapes were prepared as described in Examples 12–29, except that a woven cellulose acetate taffeta (backing used in DURAPORE surgical tape, 3M Company, St. Paul, Minn.) was substituted for the nonwoven polyester/rayon backing and the coating weight was about 58.6 g/m². UV curing conditions were not optimized.

The resulting adhesive tapes (Examples 30–46) were subsequently evaluated for skin adhesion and MVTR according to the test protocols described herein. The composition of the PSA polymer mixtures and the results of skin adhesion and MVTR evaluations are provided in Table 3. Also provided in Tables 3 are the results of testing the commercial DURAPORE surgical tape (Comparative Example 4) and 3M Cloth Adhesive Tape, Product No. 2950

(Comparative Example 5), both available from 3M Company, St. Paul, Minn.

Observations

The initial adhesions, both wet and dry of all of these examples are all >1 N/dm, and are higher than the Comparative Examples.

TABLE 3

PSA Polymer Mixtures and Corresponding Adhesive Tapes
(Woven Cellulose Acetate Backing) Skin Adhesion and MVTR Results

|    |                         |           | Tapes       | Tapes: Skin Adhesion (N/dm) | | | |
| --- | --- | --- | --- | --- | --- | --- | --- |
|    | PSA Polymer Mixtures    |           | MVTR        | $T_0$ | $T_0$ | $T_0$ (Wet)/ | $T_{48}$ |
| Ex. | Components            | Comp.     | (g/m²/24 hr) | (Dry) | (Wet) | $T_0$ (Dry) | (Dry) |
| 30 | PSA B/AC 210            | 80/20     | 752   | 3.86  | 2.35 | 0.61 | 16.37 |
| 31 | PSA B/AC 210/MPEG       | 90/5/5    | 1121  | 5.75  | 2.35 | 0.41 | 15.02 |
| 32 | PSA B/AC 210/MPEG       | 75/20/5   | 970   | 8.45  | 4.67 | 0.55 | 17.29 |
| 33 | PSA B/AC 210/MPEG       | 80/10/10  | 1369  | 8.41  | 3.20 | 0.38 | 14.86 |
| 34 | PSA B/AC 210/MPEG/ECR 180 | 70/8/8/14 | 1030 | 10.81 | 5.13 | 0.47 | 10.62 |
| 35 | PSA B/AC 210/MPEG/FORAL 85 | 70/8/8/14 | 1279 | 11.97 | 7.91 | 0.66 | 9.03 |
| 36 | PSA B/AC 315            | 90/10     | 571   | 2.62  | 1.43 | 0.55 | 11.73 |
| 37 | PSA B/AC 315/ECR 180    | 70/15/15  | 406   | 1.89  | 1.43 | 0.76 | 8.45 |
| 38 | PSA B/AC 315/ECR 180    | 70/15/15  |       | 2.01  | 1.24 | 0.62 | 7.03 |
| 39 | PSA B/AC 315/MPEG       | 60/20/20  | 1271  | 7.84  | 2.66 | 0.34 | 9.84 |
| 40 | PSA B/AC 315/MPEG       | 90/5/5    | 692   | 5.75  | 2.97 | 0.52 | 17.06 |
| 41 | PSA B/AC 315/MPEG       | 70/10/20  |       | 10.23 | 6.91 | 0.68 | 11.00 |
| 42 | PSA B/AC 315/MPEG       | 80/10/10  |       | 9.11  | 3.51 | 0.39 | 15.13 |
| 43 | PSA B/AC 315/MPEG       | 60/20/20  |       | 7.37  | 3.44 | 0.47 | 9.73 |
| 44 | PSA B/AC 315/MPEG/ECR 180 | 70/8/8/14 |     | 8.18  | 1.62 | 0.20 | 8.41 |
| 45 | PSA B/AC 315/MPEG/FORAL 85 | 70/8/8/14 |    | 12.08 | 6.29 | 0.52 | 11.50 |
| 46 | PSA B/AC 315/FORAL 85   | 70/15/15  |       | 4.32  | 1.54 | 0.36 | 8.92 |
| C4 | DURAPORE Surgical Tape  |           | 541   | 3.47  | 1.62 | 0.47 | 10.23 |
| C5 | 3M Cloth Adhesive Tape  |           | 63    | 1.51  |      |      | 2.74 |

Examples 47–64 and Comparative Examples 6 and 7

Preparation of PSA Mixtures and Corresponding Adhesive Tapes

A series of hot-melt polyacrylate PSA polymer mixtures and corresponding adhesives tapes were prepared as described in Examples 1–11, except that a woven cellulose acetate taffeta backing used in DURAPORE surgical tape (by 3M Company, St. Paul, Minn.) was substituted for the nonwoven polyester/rayon backing and the coating weight was about 58.6 g/m².

The resulting adhesive tapes (Examples 47–64) were subsequently evaluated for skin adhesion, tape gentleness, MVTR, and porosity according to the test protocols described herein. The composition of the PSA polymer mixtures and the results of the evaluations are reported in Table 4. Also provided in Table 4 are the results of testing the woven cellulose acetate taffeta backing with only a PSA A coating (Comparative Example 6) and testing DURAPORE surgical tape (Comparative Example 7), MICROPORE surgical tape (Comparative Example 8), BLENDERM surgical tape (Comparative Example 9), and 3M cloth adhesive tape (Comparative Example 10) all of which are available from 3M Company. It is noted that examples listed with identical PSA polymer mixture compositions (e.g., Examples 47 and 57) represent separately prepared and evaluated adhesives and corresponding adhesive tapes.

Observations

Initial adhesions both wet and dry are all >0.8 N/dm, and the wet/dry initial adhesion ratios are nearly all >0.80. All tapes are moderately gentle to very gentle, and are more gentle than Comparative Examples 9 and 10.

TABLE 4

PSA Polymer Mixtures and Corresponding Adhesive Tapes
(Woven Cellulose Acetate Backing)
Tape Gentleness, Skin Trauma, MVTR, and Porosity Results

| Ex. | PSA Polymer Mixtures PSA A/AC 315/MPEG Composition | MVTR (g/m²/24 hr) | Por. (sec) | Tape Gentleness | $T_0$ (Dry) | $T_0$ (Wet) | $T_0$ (Wet)/ $T_0$ (Dry) | $T_{48}$ (Dry) |
|---|---|---|---|---|---|---|---|---|
| 47 | 65/5/30 | 1169 | 55 | | 1.20 | | | 7.64 |
| 48 | 90/5/5 | 592 | 235 | 2.33 | 1.97 | 1.16 | 0.59 | 9.50 |
| 49 | 60/20/20 | 948 | 76 | 1.50 | 1.58 | 1.20 | 0.76 | 6.18 |
| 50 | 77.5/17.5/5 | 608 | 122 | 2.33 | 1.47 | 1.39 | 0.95 | 8.18 |
| 51 | 68/16/16 | 663 | 203 | 2.00 | 1.81 | 1.43 | 0.79 | 8.11 |
| 52 | 77.5/5/17.5 | 829 | 91 | 2.00 | 1.66 | 1.35 | 0.81 | 8.76 |
| 53 | 77.5/17.5/5 | 632 | 142 | | 1.85 | | | 9.03 |
| 54 | 60/10/30 | 1556 | 38 | | 1.43 | | | 7.06 |
| 55 | 60/30/10 | 940 | 164 | | 1.35 | 1.20 | 0.89 | 5.75 |
| 56 | 90/5/5 | 908 | 76 | | 1.74 | | | 9.80 |
| 57 | 65/5/30 | 1019 | 68 | | 1.54 | | | 8.38 |
| 58 | 79/10.5/10/5 | 647 | 251 | 2.00 | 1.43 | 1.24 | 0.87 | 9.26 |
| 59 | 65/30/5 | 663 | 6 | | 1.24 | 1.16 | 0.94 | 6.64 |
| 60 | 65/30/5 | 639 | 197 | | 1.00 | | | 6.83 |
| 61 | 60/20/20 | | | 1.50 | | | | |
| 62 | 70/15/15 | | | 2.00 | | | | |
| 63 | 80/10/10 | | | 2.00 | | | | |
| 64 | 90/5/5 | | | 2.33 | | | | |
| C6 | 100/0/0 | 549 | 72 | 0.83 | 1.47 | 1.11 | 0.76 | 6.45 |
| C7 | DURAPORE Tape (Run 1) | 545 | 230 | 0.67 | 2.24 | 1.27 | 0.57 | 9.65 |
| C7 | DURAPORE Tape (Run 2) | 465 | >350 | 0.83 | 2.32 | | | 9.92 |
| C8 | MICROPORE Tape | 2981 | 6 | 0.00 | 0.73 | 1.24 | 1.70 | 5.13 |
| C9 | BLENDERM Tape | 16 | >350 | 2.50 | 1.58 | 0.54 | 0.34 | 1.12 |
| C10 | 3M Cloth Adhesive Tape | 63 | >350 | 4.33 | 1.51 | | | 2.74 |

Examples 65–79 and Comparative Examples 11 and 12

Preparation of PSA Mixtures and Corresponding Adhesive Tapes

A series of hot-melt polyacrylate PSA polymer mixtures and corresponding adhesive tapes were prepared as described in Examples 1–11 as part of a component mixture design experiment. Optionally added to the polymer mixtures of "PSA A" and AVALURE AC210 were the hydrophilic plasticizer MPEG 550 and/or the hydrocarbon tackifier ECR 180.

The result adhesive tapes (Examples 65–78) were subsequently evaluated for skin adhesion, tape gentleness, MVTR, and porosity according to the test protocols described herein. The composition of the PSA Polymer Mixtures and the results of the evaluations are reported in Table 5. Also provided in Table 5 are the results of testing the nonwoven polyester/rayon backing with only a PSA A coating (Comparative Example 11) and of testing the commercially available MICROPORE surgical tape (Comparative Example 12).

TABLE 5

PSA Polymer Mixtures and Corresponding Adhesive Tapes
(Polyester/Rayon Backing)
Skin Adhesion, Tape Gentleness, MVTR, and Porosity Results

| Ex. | PSA Polymer Mixtures PSA A/AC210/MPEG/ECR 180 | MVTR (g/m²/24 hr) | Por. (sec) | Tape Gentleness | $T_0$ (Dry) | $T_0$ (Wet) | $T_0$ (Wet)/ $T_0$ (Dry) | $T_{24}$ (Dry) |
|---|---|---|---|---|---|---|---|---|
| 65 | 75/11/8/6 | 1716 | 21 | 0.34 | 1.73 | 1.93 | 1.16 | 7.19 |
| 66 | 95/5/5/0 | 1872 | 109 | 1.00 | 1.31 | 1.57 | 1.20 | 6.41 |
| 67 | 80.6/10.6/3.2/5.6 | 1084 | 122 | 1.34 | 1.86 | 1.71 | 0.92 | 6.68 |
| 68 | 75/10/0/15 | 1303 | 112 | 3.00 | 1.98 | 1.96 | 0.99 | 7.17 |
| 69 | 87/5/8/0 | 1685 | 78 | 2.34 | 1.90 | 1.54 | 0.81 | 6.11 |
| 70 | 85/15/0/0 | 2418 | 43 | 1.50 | 1.73 | 2.15 | 1.24 | 6.26 |
| 71 | 75/5/8/12 | 1365 | 47 | 0.17 | 1.57 | 1.96 | 1.25 | 6.74 |
| 72 | 75/20/0/5 | 3105 | 24 | 1.34 | 2.04 | 2.54 | 1.25 | 8.49 |
| 73 | 75/18/8/0 | 8416 | 3.7 | 0.34 | 2.17 | 2.80 | 1.29 | 8.57 |
| 74 | 85/5/0/10 | 2697 | >500 | 1.17 | 1.48 | 1.77 | 1.20 | 6.68 |
| 75 | 81/5/8/6 | 2558 | 65 | 1.67 | 2.03 | 1.57 | 0.77 | 6.78 |
| 76 | 81/11/8/0 | 3514 | 181 | 0.67 | 1.86 | 1.77 | 0.95 | 7.35 |

TABLE 5-continued

PSA Polymer Mixtures and Corresponding Adhesive Tapes
(Polyester/Rayon Backing)
Skin Adhesion, Tape Gentleness, MVTR, and Porosity Results

| | PSA Polymer Mixtures | Tapes | | | Tapes: Skin Adhesion (N/dm) | | | |
|---|---|---|---|---|---|---|---|---|
| Ex. | PSA A/AC210/MPEG/ECR 180 | MVTR (g/m$^2$/24 hr) | Por. (sec) | Tape Gentleness | $T_0$ (Dry) | $T_0$ (Wet) | $T_0$ (Wet)/ $T_0$ (Dry) | $T_{24}$ (Dry) |
| 77 | 80/5/0/15 | 1818 | 69 | 1.17 | 1.56 | 1.42 | 0.91 | 6.31 |
| 78 | 90/10/0/0 | 3344 | 7.3 | 1.67 | 1.37 | 1.74 | 1.27 | 6.37 |
| 79 | 80/20/0/0 | 9603 | 2.9 | 0.00 | 1.57 | 2.80 | 1.78 | 6.56 |
| C11 | 100/0/0/0 | 1191 | >500 | 0.75 | 1.92 | 1.67 | 0.87 | 8.62 |
| C12 | MICROPORE Tape | 4167 | 2.8 | 0.00 | 0.75 | 2.12 | 2.83 | 4.27 |

Examples 80–85 and Comparative Examples 13 and 14

Preparation of PSA Mixtures and Corresponding Adhesive Tapes

A series of hot-melt polyacrylate PSA polymer mixtures and corresponding adhesive tapes were prepared as described in Examples 1–11 as part of a mixture composition variation experiment. Optionally added to the polymer mixtures of "PSA A" and AVALURE AC 210 or AC 315 was the hydrophilic plasticizer MPEG 550.

The resulting adhesive tapes (Examples 79–84) were subsequently evaluated for skin adhesion, tape gentleness, MVTR, and porosity according to the test protocols described herein. The composition of the PSA polymer mixtures and the results of the evaluations are reported in Table 6. Also provided in Table 6 are the results of testing the nonwoven polyester/rayon backing with only a PSA A coating (Comparative Example 13) and of testing the commercially available MICROPORE surgical tape (Comparative Example 14).

TABLE 6

PSA Polymer Mixtures and Corresponding Adhesive Tapes
(Polyester/Rayon Backing)
Skin Adhesion, Tape Gentleness, MVTR, and Porosity Results

| | PSA Polymer Mixtures | Tapes | | | Tapes: Skin Adhesion (N/dm) | | | |
|---|---|---|---|---|---|---|---|---|
| Ex. | PSA A/AC Cpd/MPEG Composition | MVTR (g/m$^2$/24 hr) | Por. (sec) | Tape Gentleness | $T_0$ (Dry) | $T_0$ (Wet) | $T_0$ (Wet)/ $T_0$ (Dry) | $T_{24}$ (Dry) |
| 80 | 80/20(AC 210)/0 | 9603 | 2.9 | 1.50 | 2.50 | 3.01 | 1.20 | 8.46 |
| 81 | 90/10(AC 210)/0 | 3344 | 7.3 | 1.84 | 2.04 | 2.39 | 1.17 | 7.91 |
| 82 | 90/5(AC 210)/5 | 1872 | 258 | 2.34 | 2.02 | 2.23 | 1.10 | 7.46 |
| 83 | 80/20(AC 315)/0 | 2410 | 5.7 | 1.17 | 1.51 | 1.98 | 1.31 | 7.71 |
| 84 | 90/10(AC 315)/0 | 811 | 47.3 | 1.17 | 1.85 | 1.88 | 1.02 | 7.44 |
| 85 | 90/5(AC 315)/5 | 1248 | 34.3 | 2.00 | 1.74 | 1.95 | 1.12 | 6.91 |
| C13 | 100/0/0 | 1191 | >500 | 1.75 | 1.92 | 1.67 | 0.87 | 8.62 |
| C14 | MICROPORE Tape | 4167 | 2.8 | 0.00 | 1.14 | 2.74 | 2.40 | 5.35 |

Various modifications and alterations of this invention will become apparent to those skilled in the art without departing from the scope and principles of this invention, and it should be understood that this invention is not to be unduly limited to the illustrative embodiments set forth hereinabove. All publications and patents are incorporated herein by reference to the same extent as if each individual publication or patent was specifically and individually indicated to be incorporated by reference.

What is claimed:

1. A wet-stick pressure-sensitive adhesive comprising:
   (a) a pressure-sensitive adhesive component comprising:
      (i) at least one copolymerized monoethylenically unsaturated (meth)acrylic acid ester comprising an alkyl group having at least 4 carbons on average; and
      (ii) at least one copolymerized monoethylenically unsaturated reinforcing monomer; and
   (b) a film-forming component comprising:
      (i) at least about 50 wt-%, based on the total weight of copolymerizable monomers of the film-forming component, of at least one copolymerized monoethylenically unsaturated (meth)acrylic acid ester comprising an alkyl group having less than 4 carbons on average; and
      (ii) at least one copolymerized hydrophilic acidic monomer;
   wherein the wet-stick pressure-sensitive adhesive adheres to wet skin.

2. The wet-stick pressure-sensitive adhesive of claim 1 wherein the (meth)acrylic acid ester monomer of the pressure-sensitive adhesive component has the following general formula:

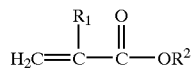

wherein R$^1$ is H or CH$_3$ and R$^2$ is a linear or branched hydrocarbon group of about 4 to about 14 carbon atoms optionally including one or more heteroatoms.

3. The wet-stick pressure-sensitive adhesive of claim 2 wherein the (meth)acrylic acid ester monomer of the pressure sensitive adhesive component is selected from the group of n-butyl acrylate, 2-ethylhexyl acrylate, isooctyl acrylate, lauryl acrylate, and mixtures thereof.

4. The wet-stick pressure-sensitive adhesive of claim 1 wherein the (meth)acrylic acid ester monomer is present in the pressure-sensitive adhesive component in an amount of about 85% wt-% to about 99 wt-%, based on the total weight of the copolymerizable monomers of the pressure-sensitive adhesive component.

5. The wet-stick pressure-sensitive adhesive of claim 1 wherein the hydrophilic acidic monomer is an ethylenically unsaturated carboxylic acid, an ethylenically unsaturated sulfonic acid, an ethylenically unsaturated phosphonic acid, or mixtures thereof.

6. The wet-stick pressure-sensitive adhesives according to claim 5 wherein the hydrophilic acidic monomer is an ethylenically unsaturated carboxylic acid.

7. The wet-stick pressure-sensitive adhesive of claim 1 wherein the hydrophilic acidic monomer is present in the film-forming component in an amount of about 1 wt-% to about 15 wt-%, based on the total weight of copolymerizable monomers of the film forming component.

8. The wet-stick pressure-sensitive adhesive of claim 1 further comprising an additive selected from the group consisting of a plasticizer, a tackifier, a pigment, glass beads, polymeric beads, fibers, a reinforcing agent, silica, a toughening agent, a fire retardant, an antioxidant, a stabilizer, or mixtures thereof.

9. The wet-stick pressure-sensitive adhesive of claim 1 which is crosslinked.

10. An article comprising a backing and a wet-stick pressure-sensitive adhesive comprising:
   (a) a pressure-sensitive adhesive component comprising:
      (i) at least one copolymerized monoethylenically unsaturated (meth)acrylic acid ester comprising an alkyl group having at least 4 carbons on average; and
      (ii) at least one copolymerized monoethylenically unsaturated reinforcing monomer, and
   (b) a film-forming component comprising:
      (i) at least about 50 wt-%, based on the total weight of copolymerizable monomers of the film-forming component, of at least one copolymerized monoethylenically unsaturated (meth)acrylic acid ester comprising an alkyl group having less than 4 carbons on average; and
      (ii) at least one copolymerized hydrophilic acidic monomer;
wherein the wet-stick pressure-sensitive adhesive adheres to wet skin.

11. The article of claim 10 which has an initial wet skin adhesion of at least about 0.8 N/dm.

12. The article of claim 10 which has an initial wet skin adhesion at least about 65% of an initial dry skin adhesion.

13. The article of claim 10 wherein the (meth)acrylic acid ester monomer is present in the pressure-sensitive adhesive component in an amount of about 85 wt-% to about 99 wt-%, based on the total weight of copolymerizable monomers of the pressure-sensitive adhesive component.

14. The article of claim 10 wherein the hydrophilic acidic monomer is present in the film-forming component in an amount of about 1 wt-% to about 15 wt-%, based on the total weight of copolymerizable monomers of the film-forming component.

15. A method of making a wet-stick pressure-sensitive adhesive, the method comprising combining under conditions for polymerization;
   (i) at least one monoethylenically unsaturated (meth)acrylic acid ester comprising an alkyl group having at least 4 carbons on average;
   (ii) at least one monoethylenically unsaturated reinforcing monomer;
   (iii) at least about 50 wt-%, based on the total weight of (iii) and (iv), of at least one monoethylenically unsaturated (meth)acrylic acid ester comprising an alkyl group having less than 4 carbons on average; and
   (iv) at least one hydrophilic acidic monomer, wherein at least (i) and (ii) or (iii) and (iv) are polymerized prior to combining (iii) and (iv) or (i) and (ii), respectively;
wherein the wet-stick pressure-sensitive adhesive adheres to wet skin.

16. The method of claim 15 wherein the at least one copolymerized monoethylenically unsaturated (meth)acrylic acid ester comprising an alkyl group having less than 4 carbons on average and the at least one copolymerized hydrophilic acidic monomer are copolymerized prior to the addition of at least one monoethylenically unsaturated (meth)acrylic acid ester comprising an alkyl group having at least 4 carbons on average and at least one copolymerized monoethylenically unsaturated reinforcing monomer.

17. A method of using an adhesive article, the method comprising:
   providing an adhesive article comprising a backing and a wet-stick pressure-sensitive adhesive layer disposed on at least one surface of the backing, wherein the wet-stick pressure-sensitive adhesive comprises:
      (a) a pressure-sensitive adhesive component comprising:
         (i) at least one copolymerized monoethylenically unsaturated (meth)acrylic acid ester comprising an alkyl group having at least 4 carbons on average; and
         (ii) at least one polymerized monoethylenically unsaturated reinforcing monomer; and
      (b) a film-forming component comprising:
         (i) at least about 50 wt-%, based on the total weight of copolymerizable monomers of the film-forming component, of at least one copolymerized monoethylenically unsaturated (meth)acrylic acid ester comprising an alkyl group having less than 4 carbons on average; and
         (ii) at least one copolymerized hydrophilic acidic monomer; and
   adhering the adhesive article to wet skin.

18. A wet-stick pressure-sensitive adhesive comprising:
   (a) a pressure-sensitive adhesive component comprising:
      (i) at least one copolymerized monoethylenically unsaturated (meth)acrylic acid ester comprising an alkyl group having at least 4 carbons on average; and
      (ii) at least one copolymerized monoethylenically unsaturated reinforcing monomer, and
   (b) a film-forming component comprising:
      (i) at least about 50 wt-%, based on the total weight of copolymerizable monomers of the film-forming component, of at least one copolymerized monoethylenically unsaturated (meth)acrylic acid ester comprising an alkyl group having less than 4 carbons on average; and
      (ii) at least one copolymerized hydrophilic acidic monomer;
wherein the wet-stick pressure-sensitive adhesive adheres to wet skin with an initial wet skin adhesion of at least about 0.8 N/dm, which is at least about 65% of an initial dry skin adhesion.

19. A wet-stick pressure-sensitive adhesive comprising:
   (a) a pressure-sensitive adhesive component comprising:
      (i) at least one copolymerized monoethylenically unsaturated (meth)acrylic acid ester comprising an alkyl group having at least 4 carbons on average that is present in an amount of about 85 wt-% to about 99 wt-%, based on the total weight of the copolymerizable monomers of the pressure-sensitive adhesive component; and
(ii) at least one copolymerized monoethylenically unsaturated reinforcing monomer that is present in an amount of about 1 wt-% to about 15 wt-%, based on the total weight of the copolymerizable monomers of the pressure-sensitive adhesive component; and
(b) a film-forming component comprising:
(i) at least one copolymerized monoethylenically unsaturated (meth)acrylic acid ester comprising an alkyl group having less than 4 carbons on average that is present in an amount of about 50 wt-% to about 99 wt-%, based on the total weight of the copolymerizable monomers of the film-forming component; and
(ii) at least one copolymerized hydrophilic acidic monomer that is present in an amount of about 1 wt-% to about 50 wt-%, based on the total weight of the copolymerizable monomers of the film-forming component;
wherein the wet-stick pressure-sensitive adhesive adheres to wet skin.

20. An article comprising a backing and a wet-stick pressure-sensitive adhesive
(a) a pressure-sensitive adhesive component comprising:
(i) at least one copolymerized monoethylenically unsaturated (meth)acrylic acid ester comprising an alkyl group having at least 4 carbons on average; and
(ii) at least one copolymerized monoethylenically unsaturated reinforcing monomer; and
(b) a film-forming component comprising:
(i) at least about 50 wt-%, based on the total weight of copolymerizable monomers of the film-forming component, of at least one copolymerized monoethylenically unsaturated (meth)acrylic acid ester comprising an alkyl group having less than 4 carbons on average; and
(ii) at least one copolymerized hydrophilic acidic monomer;
wherein the article comprises a wet-stick pressure-sensitive adhesive that adheres to wet skin with an initial wet skin adhesion of at least about 0.8 N/dm, which is at least about 65% of an initial dry skin adhesion.

21. An article comprising a backing and a wet-stick pressure-sensitive adhesive comprising:
(a) a pressure-sensitive adhesive component comprising:
(i) at least one copolymerized monoethylenically unsaturated (meth)acrylic acid ester comprising an alkyl group having at least 4 carbons on average that is present in an amount of about 85 wt-% to about 99 wt-%, based on the total weight of the copolymerizable monomers of the pressure-sensitive adhesive component; and p2 (ii) at least one compolymerized monoethylenically unsaturated reinforcing monomer that is present in an amount of about 1 wt-% to about 15 wt-% based on the total weight of the copolymerizable monomers of the pressure-sensitive adhesive component; and
(b) a film-forming component comprising:
(i) at least one copolymerized monoethylenically unsaturated (meth)acrylic acid ester comprising an alkyl group having less than 4 carbons on average that is present in an amount of about 50 wt-% to about 99 wt-%, based on the total weight of the copolymerizable monomers of the film-forming component; and
(ii) at least one copolymerized hydrophilic acidic monomer that is present in an amount of about 1 wt-% to about 50 wt-%, based on the total weight of the copolymerizable monomers of the film-forming component;
wherein the article comprises a wet-stick pressure-sensitive adhesive that adheres to wet skin.

* * * * *

UNITED STATES PATENT AND TRADEMARK OFFICE
CERTIFICATE OF CORRECTION

PATENT NO. : 6,441,092 B1
DATED : August 27, 2002
INVENTOR(S) : Melinda B. Gieselman It is certified that error appears in the above-identified patent and that said Letters Patent is hereby corrected as shown below:

Column 2,
Line 42, delete "calorimetry" and insert in place thereof -- calorimetry. --

Column 13,
Lines 23 and 27, delete "25±2" and insert in place thereof -- 24 +/- 2 --.

Column 16,
Line 49, delete "700 ml" and insert in place thereof -- 700 mJ --.

Column 27,
Line 27, delete "adhesive" and insert in place thereof -- adhesive comprising: --.

Column 28,
Line 17, delete "p2".

Signed and Sealed this

Thirteenth Day of April, 2004

JON W. DUDAS
*Acting Director of the United States Patent and Trademark Office*